(12) United States Patent
Azocar

(10) Patent No.: US 9,480,830 B1
(45) Date of Patent: Nov. 1, 2016

(54) ASSEMBLY FOR TISSUE OXYGENATION AND METHOD OF USE

(71) Applicant: Jose Azocar, Hartford, CT (US)

(72) Inventor: Jose Azocar, Hartford, CT (US)

(*) Notice: Subject to any disclaimer, the term of this patent is extended or adjusted under 35 U.S.C. 154(b) by 181 days.

(21) Appl. No.: 14/254,003

(22) Filed: Apr. 16, 2014

Related U.S. Application Data

(60) Provisional application No. 61/812,277, filed on Apr. 16, 2013, provisional application No. 61/934,977, filed on Feb. 3, 2014.

(51) Int. Cl.
| | | |
|---|---|---|
| *A61M 37/00* | (2006.01) | |
| *A61M 1/00* | (2006.01) | |
| *A61F 13/00* | (2006.01) | |
| *A61M 27/00* | (2006.01) | |
| *A61M 5/00* | (2006.01) | |
| *A61M 35/00* | (2006.01) | |

(52) U.S. Cl.
CPC ......... *A61M 37/00* (2013.01); *A61F 13/00068* (2013.01); *A61F 2013/00089* (2013.01); *A61M 1/009* (2014.02); *A61M 1/0058* (2013.01); *A61M 27/00* (2013.01); *A61M 35/00* (2013.01); *A61M 2005/006* (2013.01); *A61M 2037/0007* (2013.01)

(58) Field of Classification Search
CPC ............... A61M 37/00; A61M 35/00; A61M 2037/0007; A61M 27/00; A61M 1/0088; A61M 1/009; A61M 2005/006; A61M 1/0058; A61F 13/00068; A61F 2013/00089
See application file for complete search history.

(56) References Cited

U.S. PATENT DOCUMENTS

| | | |
|---|---|---|
| 4,113,652 A | 9/1978 | Yoshikawa et al. |
| 4,287,995 A | 9/1981 | Moriya |
| 4,365,831 A | 12/1982 | Bourne |
| 4,510,162 A | 4/1985 | Nezat |
| 4,536,409 A | 8/1985 | Farrell |
| 4,702,966 A | 10/1987 | Farrell et al. |
| 4,752,091 A | 6/1988 | Jackson |
| 5,310,497 A | 5/1994 | Ve Speer et al. |
| 5,399,289 A | 3/1995 | Speer et al. |
| 6,343,948 B1 | 2/2002 | Nutzel |
| 6,479,160 B1 | 11/2002 | Tsai et al. |
| 6,607,795 B1 | 8/2003 | Yang et al. |
| 6,709,724 B1 | 3/2004 | Teumac et al. |
| 6,772,807 B1 | 8/2004 | Tang |
| 6,821,594 B2 | 11/2004 | Watanabe et al. |
| 6,846,025 B2 | 1/2005 | Sclater et al. |
| 7,922,678 B2 * | 4/2011 | Hovorka ............... A61G 10/00 602/13 |
| 2007/0141128 A1 * | 6/2007 | Blott ................... A61M 1/0058 424/445 |

(Continued)

OTHER PUBLICATIONS

Svensjö, Tor, et al. "Accelerated healing of full-thickness skin wounds in a wet environment." Plastic and reconstructive surgery 106.3 (2000): 602-612.*

*Primary Examiner* — Imani Hayman
*Assistant Examiner* — Nilay Shah
(74) *Attorney, Agent, or Firm* — Doherty, Wallace, Pillsbury + Murphy, P.C.

(57) ABSTRACT

An assembly used to promote wound healing through the creation of an oxygen gradient, whereby the oxygen gradient hastens the diffusion of oxygen from underlying capillaries and subcutaneous tissue up through and over an overlying target site of skin tissue. In an exemplary embodiment, the assembly provides a flush cycle and/or a negative pressure cycle to enhance the flow of oxygen from the subcutaneous tissue and the capillaries to the target site. In an exemplary embodiment, the assembly further comprises a means for maintaining a constant relative humidity over the wound site.

4 Claims, 9 Drawing Sheets

(56) References Cited

U.S. PATENT DOCUMENTS

2008/0058684 A1* 3/2008 Ugander ............... A61F 13/36 601/6

2014/0336564 A1* 11/2014 Felding ............. A61F 13/00068 604/23

* cited by examiner

ASSEMBLY FOR TISSUE OXYGENATION AND METHOD OF USE

BACKGROUND OF THE INVENTION

1. Field of the Invention

The present invention relates to medical devices and processes for the promotion of the healing of skin tissue by increasing the amount of oxygen to which the skin tissue is exposed.

2. Background of the Invention

The integrity of local skin microcirculation and appropriate levels of skin oxygenation are critical factors in the maintenance of tissue integrity and in the promotion of wound healing. A common method used to increase skin tissue oxygenation involves hyperbaric oxygen therapy ("HBOT"). However, although HBOT may be efficient in some instances in increasing tissue oxygenation, it remains a cumbersome treatment option, and its use is limited to no more than a few hours per week. Additionally, some observed side effects resulting from use of HBOT may include ear and sinus trauma, oxygen toxicity to the central nervous system and to pulmonary tissue, and acceleration of cataract maturation.

Accordingly, what is needed is a cost effective alternative that increases oxygenation of the skin and subcutaneous tissue to promote wound healing, and which reduces the risk of the occurrence of certain side effects associated with the use of HBOT-based treatment methods.

SUMMARY OF INVENTION

The tissue oxygenation device ("TOD") of the present invention, and its method of use, are intended to increase tissue oxygen concentration in the skin and subcutaneous tissue of a wound site to thereby promote healing. The resulting increase in tissue oxygenation produced by the TOD promotes wound healing, especially in chronic or difficult to heal wounds, as seen in, e.g., poorly controlled diabetes (Diabetic Foot), peripheral vascular diseases, and pressure ulcers.

When properly applied and used, the TOD promotes the formation of an oxygen gradient to increase the flow of oxygen through and over a desired area of skin tissue (the "target site"), e.g., over a wound site, via the diffusion of oxygen from the subcutaneous tissue and capillary bed which closely underlie the target site. The TOD is shaped to fit the contours of a target site, i.e., the area of skin tissue through and over which an increase in oxygenation is desired, such as, for example, where there is a skin lesion or wound site, and to enclose such target site within a chamber under seal so as to isolate the target site from the ambient air. No physical contact is needed between the chamber of the TOD and the target site.

Accordingly, the chamber of the TOD is designed to enclose the target site in a substantially air tight manner such that, when the TOD is properly applied and used, in such a way that no air exchange can occur between the interior of the chamber and the outside environment. In an exemplary embodiment, the TOD comprises an outermost gas impermeable encasement which provides a substantially air-tight barrier between the target site and the ambient air, i.e., the air surrounding an exterior side wall of the encasement. Additionally, the TOD may further comprise a cuff which assists in attaching the proximal end of the TOD to the target site, and which also assists in sealing the target site within the chamber. In an exemplary embodiment, the cuff allows the TOD to be securely fitted and sealed to a variety of sized and shaped users; accordingly, a circumference of the seal is variable.

An oxygen gradient, which enhances the flow of oxygen from the subcutaneous tissue and the capillary bed to the target site, may be established by removing oxygen from the chamber. The oxygen may be initially removed or purged by configuring the TOD to allow for the controlled flow of at least one of a gas such as nitrogen, and any other oxygen removing gas which does not affect the effectiveness of the TOD in and out of the chamber. This steady and continuous removal of oxygen from the chamber, along with the substantially air tight seal created around the chamber, creates a very low oxygen concentration or oxygen free environment inside the chamber. The differences in oxygen concentration between the subcutaneous tissue and the low oxygen or oxygen-free area outside the skin contained in the chamber promotes the natural diffusion of oxygen from the capillary bed of the subcutaneous tissue closely surrounding the target site, and through, out, and over the overlying skin tissue.

To assist in detecting and monitoring the oxygen levels inside the chamber when the TOD is properly positioned over the target site and used, one or more oxygen chamber sensors may be fitted onto the TOD and placed in communication with a data processing and viewing system, such as a computer and monitor. To detect and monitor skin tissue oxygenation, and/or skin temperature, one or more tissue oxygenation sensors and/or skin temperature sensors, may be fitted onto the TOD and placed in communication with the data processing and viewing system.

In an exemplary embodiment, the TOD is integrated into an assembly further comprising members comprising a tubing subassembly, an oxygen depleting gas source, such as, e.g., nitrogen; a pump, an oxygen sensor, a pressure sensor, a gas temperature/humidity sensor, and a moisture absorption canister, wherein the members are in fluid communication with one another and with the wound site inside the TOD, and wherein the gas emitted from the oxygen depleting gas source moves through the system in a manner which efficiently removes oxygen from the area of the TOD surrounding the wound site thereby creating an oxygen gradient from the capillary bed of the subcutaneous tissue towards the skin, thereby promoting wound healing. In addition, one or more oxygen scavenger components may be part of the TOD, to remove oxygen from the chamber, in order to keep a low oxygen concentration within the chamber.

The disclosure provides by way of example, an exemplary assembly for tissue oxygenation, comprising a tissue oxygenation device (TOD) comprising a chamber formed within an encasement, wherein the chamber is formed to enclose a wound site; an oxygen depleting gas; a valve located upstream of the chamber; an oxygen sensor located downstream of the chamber; a pressure sensor located downstream of the chamber; a pump located downstream of the chamber, wherein the pump provides a force which moves the oxygen depleting gas through the assembly; another valve located downstream of the pump, and which, depending on the oxygen concentration within the chamber, directs the oxygen depleting gas out of the assembly or back to the chamber; and a tubing subassembly which provides a conduit through which the oxygen depleting gas and the depleted oxygen flows through the assembly.

Another exemplary assembly for tissue oxygenation comprises a tissue oxygenation device comprising a chamber formed within an encasement; an oxygen depleting gas; a first valve located upstream of the chamber; a moisture absorption canister; a housing having disposed therein an oxygen sensor and a pressure sensor, wherein the housing is located downstream of the moisture absorption canister; a second valve located downstream of the chamber and which, depending on the relative humidity of the oxygen depleting gas as determined by the pressure sensor, directs the oxygen depleting gas towards either the moisture absorption canister or the housing; a pump located downstream of the housing, wherein the pump provides a force necessary to move the oxygen depleting gas through the assembly; a third valve located downstream of the pump, wherein, depending on at least one of the oxygen concentration in the chamber and the pressure in the chamber, the third valve either directs the oxygen depleting gas out of the assembly or recycles the oxygen depleting gas through the assembly; and a tubing subassembly which provides a conduit through which the oxygen depleting gas flows through the assembly and towards and through the chamber, the first valve, the moisture absorption canister, the housing, the second valve, the pump, and the third valve.

An exemplary method for promoting tissue oxygenation disclosed herein comprises providing an assembly, comprising: a tissue oxygenation device, wherein the tissue oxygenation device comprises a chamber formed within an encasement; a first valve, a second valve, a pump, and a tubing subassembly, wherein the tubing subassembly provides a conduit through which an oxygen depleting gas flows through the assembly to deplete the oxygen present within the encasement. The method further includes applying the tissue oxygenation device to the extremity where the wound is located. The method further includes providing a flush cycle. During the flush cycle oxygen is removed from the chamber of the tissue oxygenation device. The flush cycle comprises maneuvering the first valve to allow entry of the oxygen depleting gas into the tubing subassembly from the source; actuating the pump to thereby draw the oxygen depleting gas through the first valve and into the chamber via the tubing subassembly, and to further thereby purge the oxygen from the chamber and through the second valve via the tubing subassembly; and maneuvering the second valve to allow exit or displacement of the oxygen from the chamber. After a few seconds, or a few minutes (according to the size of the chamber), the oxygen is depleted from the chamber.

Once the oxygen concentration in the chamber has reached a threshold value (e.g., less than about 2%) the flush cycle includes recirculating the oxygen depleting or low oxygen gas through the system. Recirculating may comprise maneuvering the first valve to prevent the oxygen depleting gas from entering the assembly from the source; maneuvering the second valve such that the oxygen depleting gas is not vented out from the assembly; and actuating the pump thereby causing the oxygen depleting gas to flow the system. In this manner, an oxygen depleted or low oxygen environment is formed inside the chamber containing the wound site, wherein such a reduced oxygen concentration promotes the formation of an oxygen gradient or diffusion of oxygen from the capillaries and subcutaneous tissue surrounding the wound site.

The method may further comprise a negative pressure cycle which includes creating a negative pressure in the chamber. In an exemplary embodiment, creation of a negative pressure comprises: maneuvering the first valve to prevent entry of the oxygen depleting gas into the assembly via the source; maneuvering the second valve to allow the oxygen depleting gas to exit the assembly; and actuating the pump to form the negative pressure. In an exemplary embodiment, the negative pressure created in the chamber during the negative pressure cycle is from about −5 millimeters of mercury ("mmHg") to about −25 mmHg.

The exemplary method may further comprise providing the assembly which further includes a third valve, a moisture absorption canister, and a humidity sensor, and further passing the oxygen depleting gas over the humidity sensor so that the relative humidity may be detected and recorded; determining whether the relative humidity exceeds a threshold level; manipulating a third valve so that the oxygen depleting gas passes through the moisture absorption canister when the relative humidity exceeds the threshold level; and manipulating the third valve so that the oxygen depleting gas bypasses the moisture absorption canister when the relative humidity does not exceed the threshold level.

DETAILED DESCRIPTION OF THE INVENTION

Figure 1:
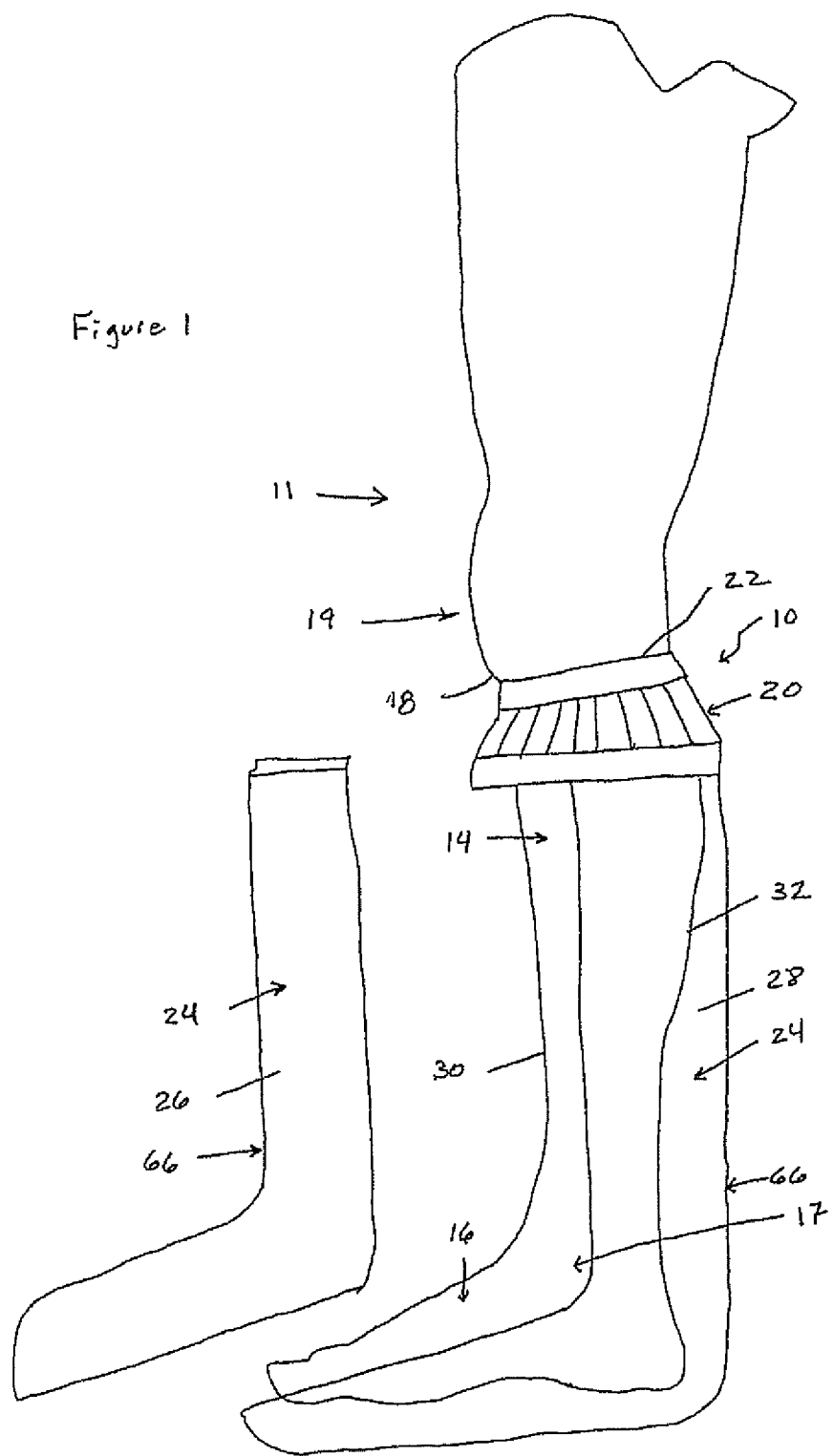
FIG. 1 is a schematic depicting an exemplary embodiment of a below the knee TOD.

Supplying oxygen to skin tissue in need of oxygen for therapeutic purposes, such as in the case of skin lesions in diabetic foot ulcers, peripheral vascular diseases, and other situations where the circulation and/or the source of oxygen is compromised, is essential to wound healing. The TOD of the present invention increases the amount of oxygen over a target site of skin tissue by taking advantage of Fick's First Law of Diffusion ("Fick's Law"), along with the fact that skin tissue is semipermeable to oxygen. Were Fick's law to be applied to the function of this dynamic TOD, and, hence upheld, this would further prove the ability of the newly designed protocol to increase skin oxygenation. The direction of the oxygen rate of diffusion can be determined using Fick's equation, where the volume of oxygen flow moving across the skin per unit of time ($V_{O2}$) is directly proportional to the area of the skin involved and to the difference in the partial pressures of oxygen between the two sides, but is inversely proportional to the tissue thickness:

$$\text{Rate of diffusion}\,(\dot{V}_{O2}) = \frac{D \cdot A \cdot (P_2 - P_1)}{X}$$

where D denotes the diffusion coefficient constant of oxygen and A is the surface area of the skin covered by the device (FIG. 1), where oxygen diffusion occurs. $P_2$ is the partial oxygen pressure in the subcutaneous tissue, $P_1$ is the partial oxygen pressure in the closed environment, just outside the skin, and X is the thickness of the skin. Hence, D/X=P, the permeability coefficient of oxygen in skin.

Using this formula, the flux of oxygen and the direction of its diffusion can be calculated. Therefore, pursuant to Fick's Law, the ability of oxygen to diffuse from the capillaries and subcutaneous tissue, through the skin tissue, and eventually out of the body, occurs if the concentration of oxygen outside the body is lower than the concentration of oxygen inside the body.

The TOD of the present invention, when properly applied and used, causes a constant outward diffusion of oxygen from nearby underlying blood capillaries and subcutaneous tissue, to a target skin tissue (the "target site"), and eventually out through and over the target site. Utilizing the principles of Fick's Law, again which postulates that oxygen flows from regions of high concentration to regions of low concentration in a magnitude that is proportional to the oxygen concentration gradient, the TOD of the present invention is designed to seal the target site within a chamber so that no air from outside the chamber enters the chamber of the TOD which encloses the target site.

The chamber of the TOD is formed, at least in part, by a gas impermeable encasement. The primary purpose of the gas impermeable encasement is to prevent ambient air from entering the chamber. Preferably, the gas impermeable encasement is ergonomically shaped to fit the contours of a variety of shaped and sized users. An exemplary outermost gas impermeable encasement comprises a thermoplastic polymer resin, such as a medical-grade polyvinylchloride (PVC) or polypropylene.

The TOD further comprises a gas impermeable, flexible cuff which assists in engaging and disengaging the TOD to and from the target site. The cuff also serves to create a substantially air tight seal that isolates the target site in the chamber from appreciable amounts of the ambient air. Additionally, in an exemplary embodiment, the cuff may be used to adjust the TOD to the individual size requirements of a particular user; accordingly, a circumference of the cuff may be variable.

The cuff, which may be formed from a non-synthetic or a synthetic flexible rubber material, may be attached to the gas impermeable encasement via, for example, an adhesive material. This adhesive may further be used to attach the cuff to the target site. The adhesive may be formed from a wide variety of presently known materials or from future known materials, all of which properly fixedly attach to the target site when necessary, but which are also relatively removable when necessary, and which are considered safe for application to the target site. Nevertheless, exemplary adhesive materials include without limitation, one or more of a classical pressure sensitive adhesive, a hydrocolloid PSA, a hydrogel, and the like.

In an exemplary embodiment, the TOD may also comprise at least one or more of the following an oxygen scavenging member, a barrier layer, a moisture/exudate absorbing layer, and an adhesive layer.

The oxygen scavenger removes the oxygen contained within the chamber which encloses the target area, thereby reducing the oxygen concentration within the chamber. This depletion of oxygen in the substantially air tight chamber naturally causes an oxygen concentration to decrease, hence, an increased flow of oxygen from the nearby subcutaneous tissue and capillaries, up, through and over the target site, and into the chamber (following the Fick's Law as explained above). The oxygen scavenger can be any currently known or unknown material capable of effectively removing oxygen from the chamber, which is compatible with the other component(s) of the device, and which is acceptable for use on or near the target site. For example, the oxygen scavenger may comprise one or more of oxygen scavenging powders, pellets, and the like formed from materials such as, e.g., iron and iron compounds, such as, iron sulfate.

In addition to the oxygen scavenger, the oxygen scavenging member may further comprise a thermoplastic film. An exemplary oxygen scavenging member is described in U.S. Pat. No. 5,089,323 to Nakae et al., which discloses an oxygen-absorbing sheet comprising a thermoplastic resin and an oxygen absorbent made of iron powder. Another exemplary oxygen scavenging member is described in U.S. Pat. No. 6,063,503 to Hatakeyama et al., which teaches an oxygen-absorbing multi-layer film comprising a deoxidizing resin layer containing iron powder. Another exemplary oxygen scavenger is described in U.S. Pat. No. 6,391,407 to Kashiba et al., which discloses an oxygen-absorbing layer containing an iron deoxidizing agent.

U.S. Pat. No. 6,503,587 to Kashiba et al. ("'587") discloses an oxygen-absorbing multi-layer film suitable for preserving food. Referring to FIG. 1 of '581, the multi-layer film comprises an outer layer 1 to which pigment is added; a contiguous thermoplastic resin layer 3; a gas barrier layer 4; and a protecting layer 5. Layers 3, 4, 5 may be successively laminated on layer 1. Particles of an oxygen-absorbing agent 2 (preferably, iron powder) may be locally interspersed between layers 1 and 3, with some of the particles being distributed in the interface between the adjacent layers (1 and 3) while some particles are present in one of the layers (1 or 3) and the other particles are present in both the layers (1 and 3). The disclosure of '587 is hereby incorporated in its entirety by reference.

In addition to the oxygen scavenger, the TOD may also comprise one or more types of desiccants to reduce the humidity of the chamber. Although the desiccant may be selected from a wide variety of desiccants, a preferable desiccant comprises at least one of a silica gel, Desi Paste™, which is manufactured by Sud Chemie, and the like.

The barrier layer serves to buffer the target site from the oxygen scavenging member. The barrier layer may comprise a wide range of materials so long as the barrier layer is oxygen permeable and considered safe for application to or near the target site. Additionally, in a preferred embodiment, the barrier layer is also non-absorbent. In an exemplary embodiment, the barrier layer comprises at least one of tegaderm hydrocolloid (3M), Mepitel (Molnlycke Health Care Inc) Melitex Lite Bioflex 130, Bioflex 235 (Scapa North America), and the like, wherein tegaderm hydrocolloid is especially preferred.

The moisture/exudate absorbing layer absorbs skin moisture and exudates, and in an exemplary embodiment comprises at least one of aquacel hydrofiber hydrocolloid, Mepore (Molnlycke Health Care Inc), Tegaderm THIN hydrocolloid dressing (3M), Melolite (Smith and Nephew Inc), and the like, wherein an aquacel hydrofiber hydrocolloid is especially preferred. One or more moisture/exudate absorbing layers may be used according to the volume of exudates expected to be absorbed.

The adhesive layer may be used to attach the oxygen scavenging member, and, when used, the barrier layer(s) and/or the moisture/exudate absorbing layer(s) to the gas impermeable encasement. Accordingly, the adhesive layer may be selected from a wide variety of materials so long as the materials allow the adhesive layer to be securely attached to the encasement during application of the TOD to a user, ensures that the adhesive does not affect the efficacy of the TOD, and is regarded as appropriate for use on the target site.

In an exemplary embodiment, the oxygen scavenging member and at least one or more of the barrier layer, and the moisture/exudate absorbing layer, and the adhesive layer, is formed as a multi-layered composite, and more preferably, as a multi-layered laminated composite. An exemplary lamination process may occur via the process disclosed in '587 and in U.S. Pat. No. 6,746,772 to Kashiba et al. Preferably, the composite is pliable and flexible such that the composite may be disposed on and fitted to the contours and shape of the interior side of the gas impermeable encasement.

The TOD may further comprise a means whereby the oxygen concentration in the chamber may be more quickly decreased to hasten the formation of the oxygen gradient from the capillary bed of the subcutaneous tissue and promote diffusion of oxygen molecules to the overlying nearby target/wound site. In an exemplary embodiment, such oxygen purging means may comprise a porthole formed through the gas impermeable encasement and a bivalve disposed within such porthole such that the bivalve extends out from an exterior side of the gas impermeable encasement, and extends into the chamber from the interior side of the gas impermeable encasement. The bivalve may comprise any conventionally known bivalve which is suitable for use with the TOD. Nitrogen gas, helium gas, or any other suitable gas, e.g., may be added into the chamber via the bivalve, and be used to displace the oxygen initially contained in the chamber via the bivalve.

Additionally, the TOD may be designed to allow for the detection and monitoring of oxygen concentrations within the chamber, and the oxygenation of the skin at one or more points on the target site. To that end, the gas impermeable encasement may include one or more portholes each of which may hold an oxygen chamber sensor, as known in the art, and which measures the oxygen concentration in the chamber. Additionally or alternatively, the gas impermeable encasement may include one or more portholes, each of which may hold a tissue oxygenation sensor, as known in the art, and which measures the oxygenation of the skin tissue in the area surrounding the tissue oxygenation sensor. Each sensor may be in communication with a data receiver and data detection device, such as a computer processor and a monitor, as is known, or will be known, in the art.

An exemplary method for applying the TOD to a target site comprises selecting a target site, wherein exemplary target sites include without limitation, an appendage (e.g., a hand, an arm, a foot, or a leg), a torso, and the like. The exemplary method further comprises providing the gas impermeable encasement and the cuff. In an exemplary embodiment, the gas impermeable encasement is divided into an anterior portion which is to be disposed over an anterior portion of the target site, and a posterior portion, which is to be disposed over a posterior portion of the target site. If used, the one or more composites are strategically applied to those portions of the posterior and/or the anterior portions of the encasement in order to achieve the oxygen depletion in the chamber and promote the oxygen gradient and the desired rates of oxygen diffusion from the nearby subcutaneous tissue and capillaries, and through and over the target/wound site contained within the chamber. The composite is fixed to the interior side of the gas impermeable encasement by disposing the adhesive layer of the composite directly onto the interior side. Additionally, because the composite is formed to be flexible and pliable, when attached to the encasement, the composite fits the shape and contours of the encasement. Once the optional composite has been placed on its respective anterior and/or posterior portion of the encasement, the anterior and posterior portions of the gas impermeable encasement may be placed over the respective target site.

With or without use of the composite, the anterior and posterior portions are attached to each other to form a substantially air tight seal between the two portions of the gas impermeable encasement. In a preferred embodiment, the anterior and posterior portions are sealed to create a closed distal end and an open-ended proximal end. The cuff may then be applied to the open-ended proximal end of the gas impermeable encasement to seal the target site within the chamber.

The anterior and posterior portions may be configured to form a seal pursuant to the teachings of U.S. Pat. No. 6,772,807 to Tang ("'807"), wherein such teachings are included herein by reference in their entirety. More specifically, anterior portion may be configured such as is taught by reference number 13 in '807, and posterior portion may be configured such as is taught by reference number 22 in '807, or vice versa.

Additionally, each of anterior and posterior portions may comprise complementary latching mechanisms which further assist in creating a substantially air-tight seal between the anterior and posterior portions. Exemplary latching mechanisms may include, without limitation, those such as are taught in U.S. Pat. Nos. 4,365,831; 6,343,948; 4,752,091; and 6,846,025; all of which are incorporated by reference herein in their entirety.

After application of the TOD around the target site, the chamber may be subject to one or more alternating cycles comprising an oxygen gas removing flush cycle and a negative pressure cycle, as will be described in greater detail below herein.

Exemplary embodiments of the TOD and its method of use shall now be discussed with reference to the figures, wherein it is to be understood that the figures are in no way limiting, but are provided for illustrative purposes only. As such, the invention is not to be limited to such depicted embodiments, but shall be covered under any and all variations and modifications to the depicted embodiments as would occur to one of ordinary skill in the art based upon a reading of the present disclosure.

Figure 3:
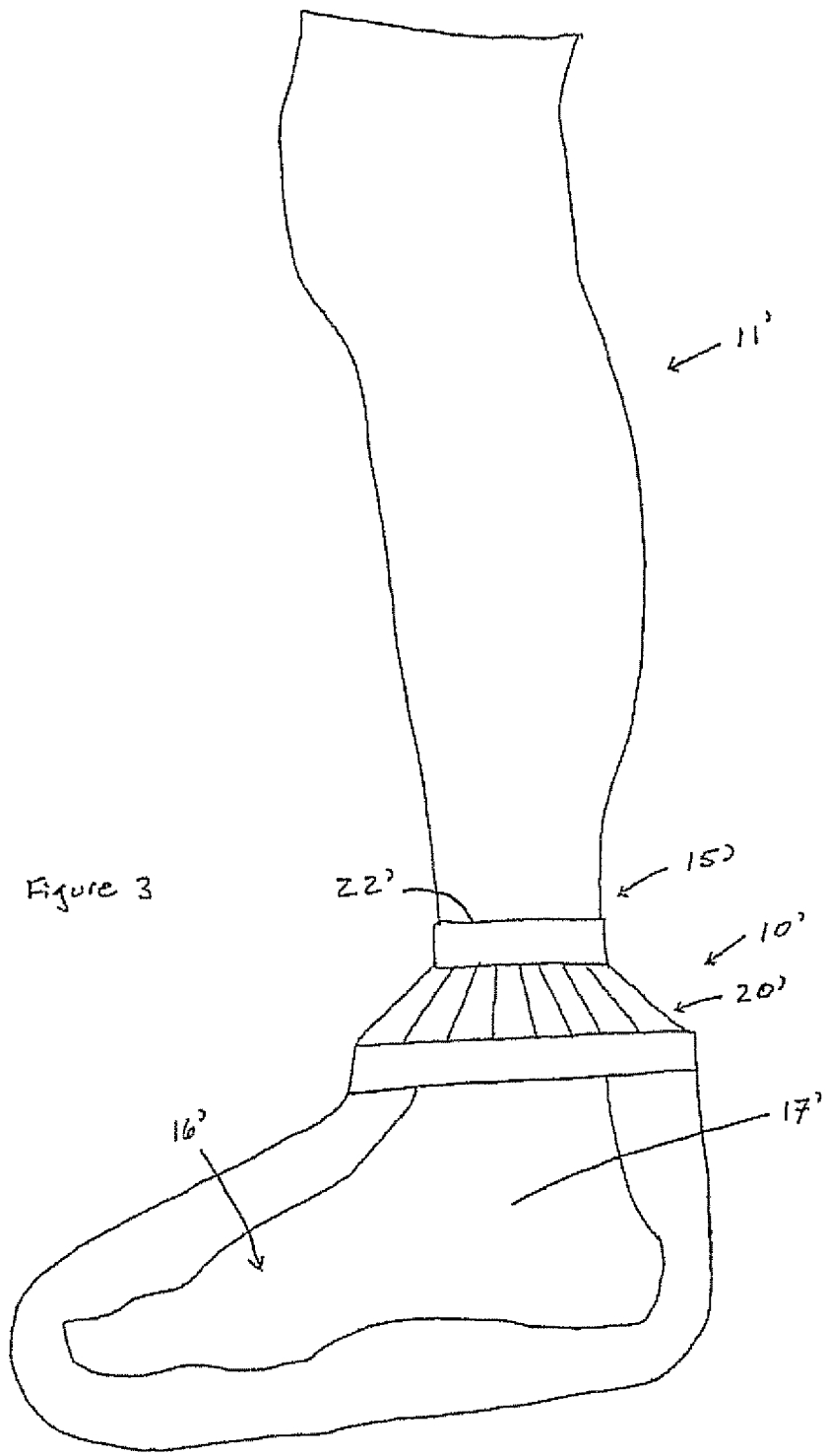
FIG. 3 is a schematic depicting another exemplary embodiment of an above the ankle TOD.

Referring to FIGS. 1 and 3, exemplary TOD 10 and TOD 10' respectively depict placement of the TOD around various appendages. More specifically, FIG. 1 depicts the placement of TOD 10 onto and around an appendage 11 comprising a lower leg 14, a foot 16, and an ankle 17 such that a top edge 22 of a cuff 20 of TOD 10 terminates at a bottom 18 of a knee 19. FIG. 3, depicts placement of TOD 10' onto and around an appendage 11' comprising a foot 16' and an ankle 17' such that a top edge 22' of a cuff 20' terminates just above ankle 17' and below a lower calf 15'. Other than the obvious differences and variations in the size and shape of TOD 10 and 10', TOD 10 and TOD 10' are identical in terms of their materials, structure, and functions. Accordingly, the remainder of the specification will be structured around a description of TOD 10, wherein it is to be understood that such description applies equally to a description of TOD 10'. It is additionally noted that TOD 10 may also be accommodated and modified in obvious ways to fit other appendages and/or body parts not depicted in the figures, including for example, all or a portion of an arm, leg, chest, neck, torso, and the like.

Figure 2:
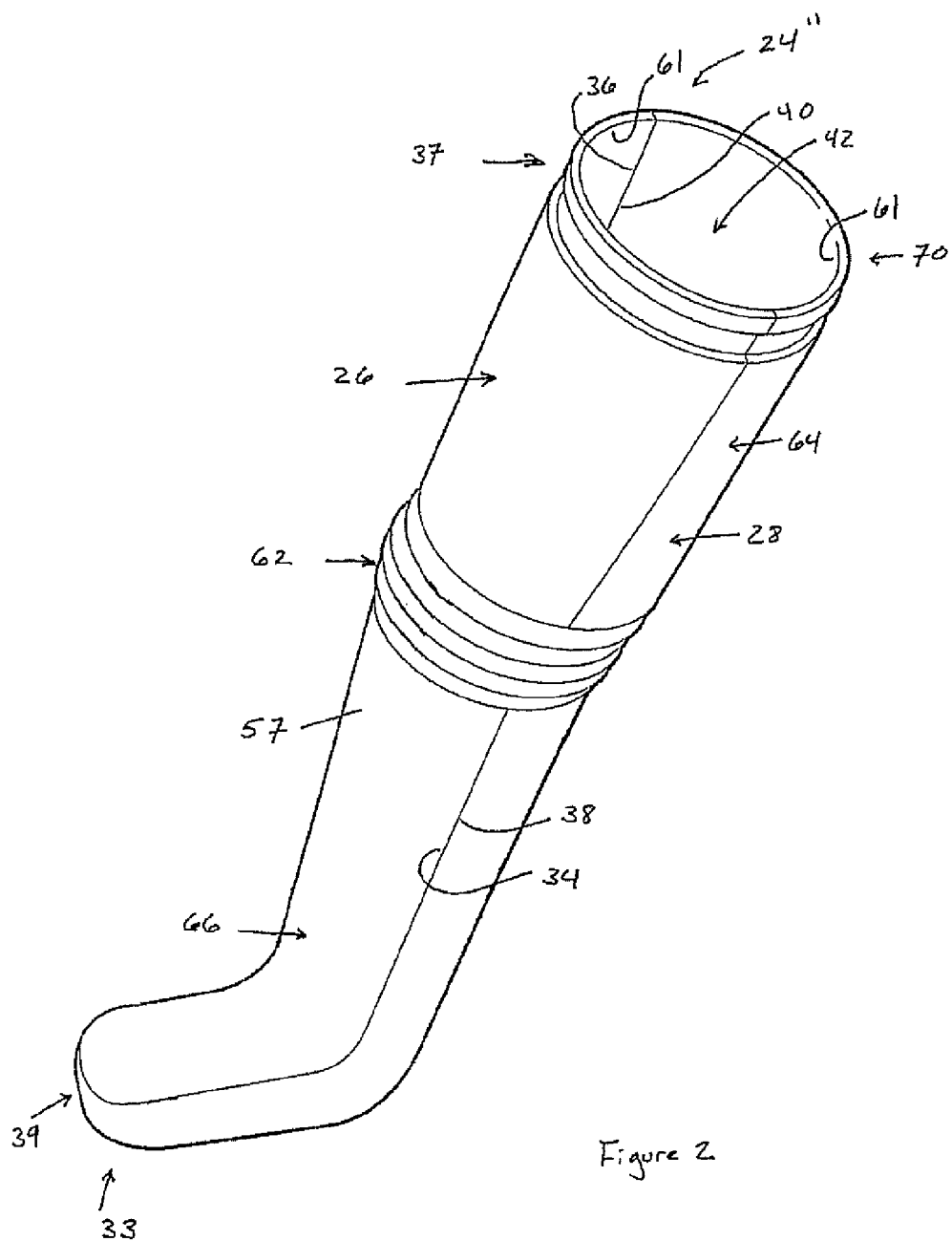
FIG. 2 is a schematic depicting an exemplary above the knee gas impermeable encasement.

FIG. 2 depicts a gas impermeable encasement 24" which is configured to fit around an appendage 11" comprising an upper leg 23, knee 19, lower leg 14, foot 16, and ankle 17. In addition to a lower member 66, which surrounds lower leg 14, foot 16, and ankle 17, gas impermeable encasement further comprises a knee adaptor 62 and an upper leg member 64, wherein knee adaptor 62 is specially configured to wrap around the knee of the target site, and upper leg member 64 is configured to wrap around the upper leg of the target site. It is noted that gas impermeable encasement 24" may be used as a component of forming a TOD having essentially the same properties and characteristics as TOD 10 and 10', where the only difference relates to size and geometrical configurations.

Figure 6:
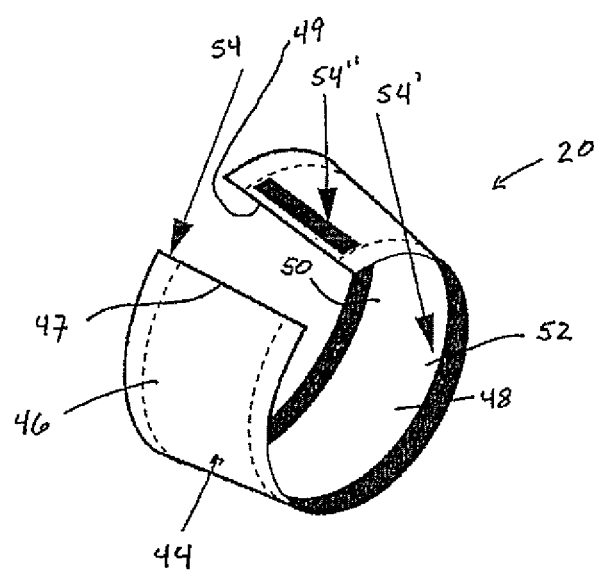
FIG. 6 is a schematic depicting an exemplary cuff of the TOD.

Referring to FIGS. 1 and 6, TOD 10 comprises cuff 20, and a gas impermeable encasement 24 which is divided into an anterior portion 26 and a posterior portion 28. Referring to FIG. 1, anterior portion 26 encloses an anterior side 30 of foot 16 and of lower leg 14, and posterior portion 28 encloses a posterior side 32 of foot 16 and of lower leg 14. Referring to FIG. 2, anterior portion 26 encloses an anterior side 30 of foot 16, lower leg 14, knee 19, and upper leg 23, and posterior portion 28 encloses a posterior side 32 of foot 16, lower leg 14, knee 19, and upper leg 23. Referring to FIGS. 1 and 2 when lateral edges 34 and 36 of anterior portion 26 are merged with lateral edges 38 and 40 of posterior portion 28, TOD 10 forms a chamber 42 which surrounds respective appendages 11 and 11'.

Figure 4:
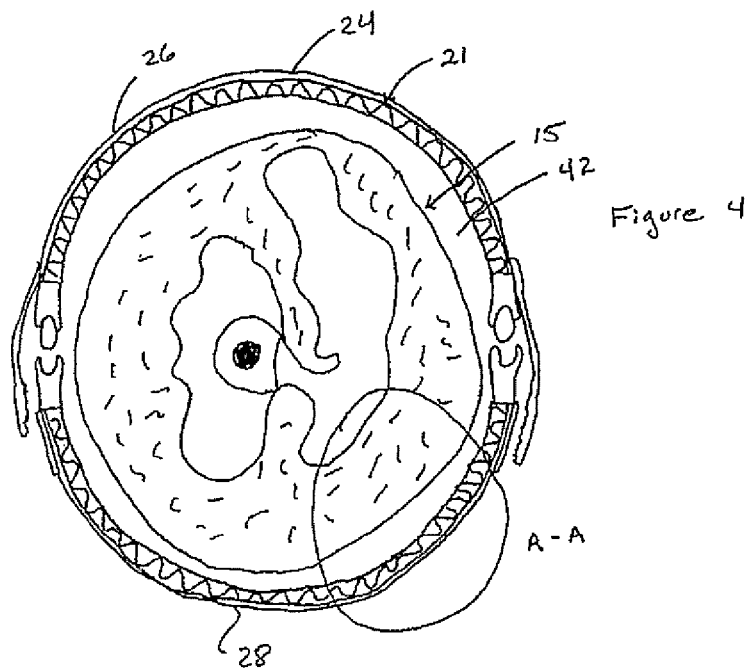
FIG. 4 is a schematic depicting a cross-sectional view of an exemplary TOD disposed around a leg target site.
Figure 5:
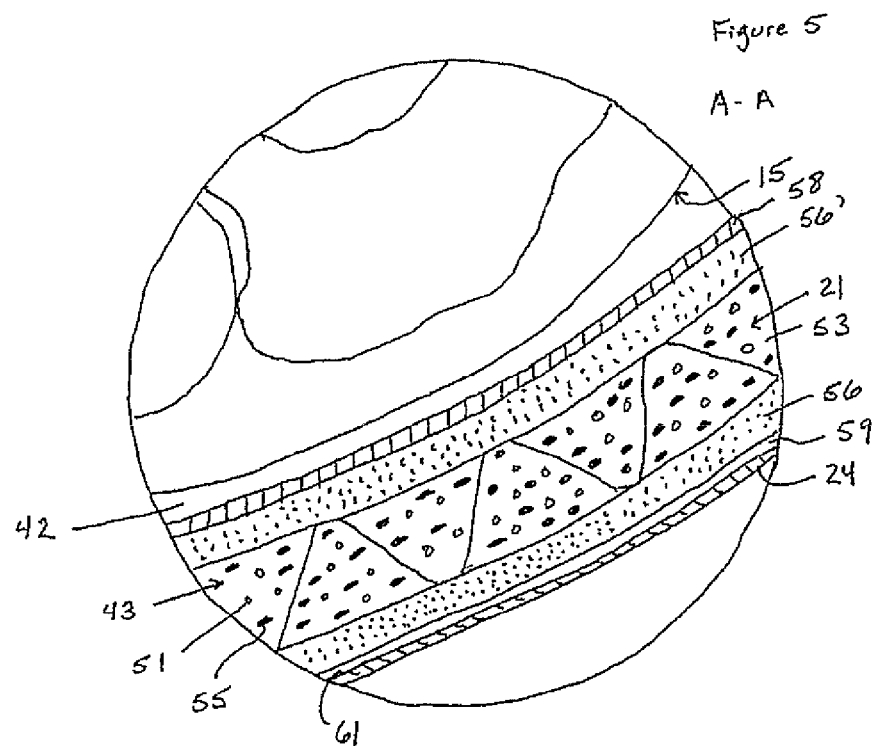
FIG. 5 is a schematic depicting a magnified section A-A of the TOD depicted in FIG. 4.

Referring to FIGS. 4 and 5, TOD 10 may further comprises an optional composite 21, which comprises an oxygen scavenging member 43, a moisture/exudate absorbing layer 56, a moisture/exudate absorbing layer 56', a barrier layer 58, and an adhesive layer 59. Adhesive layer 59 is disposed on an interior side 61 of gas impermeable encasement 24.

Referring to FIG. 5, oxygen scavenging member 43 comprises iron pellets 55 and desiccants 51 randomly distributed into a film 53

Referring to FIG. 6, cuff 20 comprises a planar body 44 having an exterior side 46 opposite to an interior side 48, and a distal terminal end 47 opposite to a proximal terminal end 49. A proximal surface 50 and a distal surface 52 of interior side 48 each has disposed along a length thereof respective double-sided adhesive strips 54 and 54'. When TOD 10 is in proper use, double adhesive strip 54 attaches to an exterior side 57 at a proximal end 37 of anterior portion 26 of gas impermeable encasement 24, and double adhesive strip 54' attaches TOD 10 to bottom 18 of knee 19.

A double adhesive strip 54" is also disposed on exterior side 46 towards proximal terminal end 49 of cuff 20. Body 44 of cuff 20 may be wrapped over onto itself such that double adhesive strip 54" attaches to interior side 48 of cuff 20 to properly fit TOD 10 to a target site 15. In addition to attaching TOD 10 around a target site, adhesive strips 54, 54', and 54" also assist in creating an air tight seal between TOD 10 and target site 15.

Figure 7:
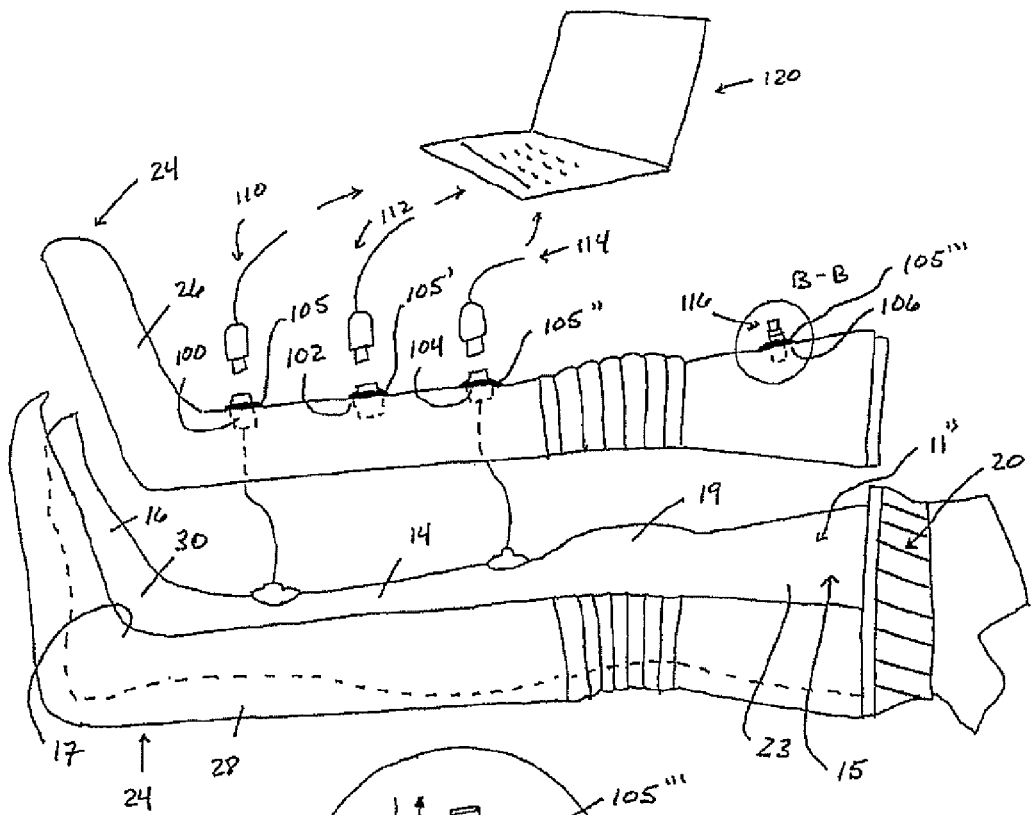
FIG. 7 is a schematic depicting an exemplary use of an exemplary TOD incorporating the gas impermeable encasement depicted in FIG. 2.

Referring to FIG. 7, in an exemplary embodiment, anterior portion 26 of gas impermeable encasement 24 has portholes 100, 102, 104, and 106 formed therethrough, wherein each of portholes 100, 102, 104, and 106 comprises a respective rubber seal 105, 105', 105", and 105'" formed around the periphery thereof. A skin oxygenation sensor 110 is disposed on target site 15 and is fitted on and through porthole 100 such that rubber seal 105 is fitted around skin oxygenation sensor 110 so that appreciable amounts of oxygen cannot enter chamber 42 through porthole 100. An oxygen chamber sensor 112 is fitted on and through porthole 102 such that rubber seal 105' is fitted around oxygen chamber sensor 112 so that appreciable amounts of oxygen from the environment outside the TOD cannot enter chamber 42 though porthole 102. A skin temperature sensor 114 is disposed on target site 15 and is fitted on and through porthole 104 such that rubber seal 105" is fitted around skin tissue temperature sensor 114 so that appreciable amounts of environmental air cannot enter chamber 42 through porthole 104. A bivalve 116 is fitted on and through porthole 106 such that rubber seal 105'" is fitted around bivalve 116 so that appreciable amounts of environmental air cannot enter chamber 42 through porthole 106.

Bivalve 116 controls the flow of gas molecules into and out from chamber 42 and/or from the ambient air. All of skin oxygenation sensor 110, oxygen chamber sensor 112, skin tissue temperature sensor 114, and bivalve 118 are in communication with a computer 120 for purposes of determining, recording, monitoring, and assessing oxygenation of the target site.

Referring to the figures, an exemplary method of using tissue oxygenation device 10 to promote diffusion of oxygen from nearby subcutaneous tissue and capillaries to target site 15 includes applying composite 21 to at least one of anterior portion 26 and posterior portion 28 of gas impermeable encasement 24 by disposing adhesive layer 59 onto interior side 61 such that composite 21 conforms to the shape and contours of interior side 61. Posterior portion 28 may then be positioned over posterior side 32 of appendage 11, and anterior portion 26 may be positioned over anterior side 30 of appendage 11. Anterior portion 26 and posterior portion 28 are then sealed to one another to create an open-end 70 at proximal end 37 of encasement 24 and a closed end 39 at a distal end 33 of encasement 24.

Cuff 20 is applied to proximal end 37 to close off open-end 70 and to seal target site 15 within chamber 42. In an exemplary embodiment, adhesive 54 is disposed on exterior side 57 at proximal end 37 of gas impermeable encasement 24, adhesive 54' is applied to bottom 18 of knee 19, and adhesive 54" is disposed on an interior side of body 44 of cuff 20 so that cuff 20 seals target site 15 within chamber 42.

Figure 8:
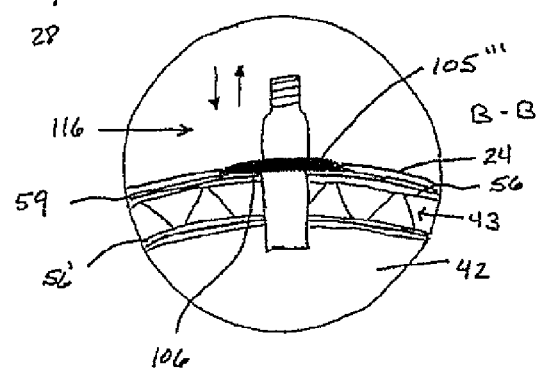
FIG. 8 is a schematic depicting a magnified section B-B from the TOD depicted in FIG. 7.

Referring to FIG. 8, in an exemplary embodiment, the method may further comprise purging chamber 42 of oxygen, wherein purging occurs at the point of initiating the process to shorten the time needed to obtain the lower oxygen concentration in the chamber which is necessary for establishing the oxygen gradient and diffusion to occur. In an exemplary embodiment, a nitrogen gas is delivered into chamber 42 through bivalve 116, while the oxygen rich air is initially contained in chamber 42 is extracted through bivalve 116.

Once tissue oxygenation device 10 is applied to the target site as set forth and described above herein, the oxygen scavenger contained in oxygen scavenging member 43 and 43', continuously and steadily removes oxygen contained within chamber 42. As this causes the oxygen concentration within chamber 42 to be lower than the oxygen concentration in the nearby subcutaneous tissue and capillaries, oxygen from the nearby subcutaneous tissue and capillaries flows through and over target site 15 and into chamber 42. As the oxygen scavenger is continuously removing oxygen from chamber 42, the diffusion of oxygen from the subcutaneous tissue and the capillaries and out into chamber 42 occurs continuously. Accordingly, the increase in oxygenation through and over the target/wound site is obtained by the continuous flow of oxygen molecules moving along the concentration gradient formed by the continuous removal of oxygen from chamber 42 by the oxygen scavenger in addition to the displacement of oxygen by purging the chamber by nitrogen.

Figure 9:
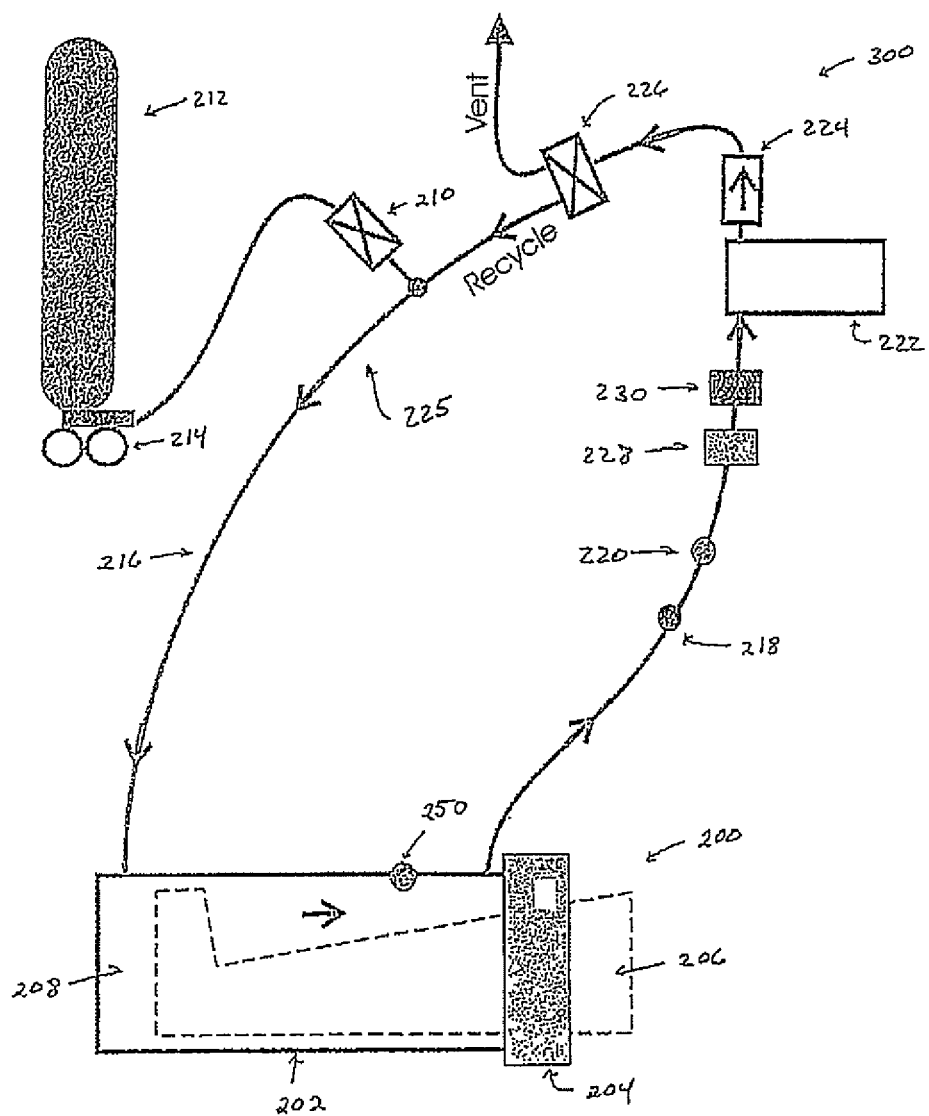
FIG. 9 is a schematic depicting an exemplary assembly and its method of use.

FIG. 9 depicts another exemplary embodiment of the tissue oxygenation device and further depicts an exemplary method of using such device. Here, an assembly 300 comprises a tissue oxygenation device 200 and a tubing subassembly 225 which forms a conduit through which an oxygen depleting gas provided from a source 212 flows through assembly 300.

Tissue oxygenation device 200 comprises an encasement 202 and a cuff 204, which have been provided over a leg 206 of a patient and which define a chamber 208. Device 200, which may or may not comprise an oxygen scavenger and/or composite as described above, is designed JO to be compatible within an assembly designed to displace the oxygen gas within chamber 208 via an oxygen removing gas, such as, for example, nitrogen, helium, and the like. The goal of assembly 300 is to establish an oxygen free or low oxygen concentration within chamber 208, and, in this way, form an oxygen gradient from the capillary bed toward the target site, i.e., leg 206. The gradient may be further enhanced by creating a low pressure, i.e., preferably between about −5 mm Hg to about −25 mm Hg in chamber 208. The oxygen molecules moving along this gradient, from the subcutaneous tissue towards the target site, result in an increase in oxygen concentration in the skin and subcutaneous tissue that promotes wound healing. The oxygen gradient may be increased further through the inhalation of oxygen.

In an exemplary embodiment, tissue oxygenation device 200 has one or more of the following characteristics and/or abilities:

- tissue oxygenation device 200 is capable of establishing and maintaining an oxygen concentration in chamber 208 of no more than up to about 2 percent ("%"), wherein the percentage is based upon the total volume of gas contained within the chamber;
- tissue oxygenation device 200 is capable of cycling pressure over the target site between ambient pressure and up to about −5 mm Hg to about −25 mm Hg for a minimum of about 15 minutes to about 20 minutes for each cycle over a minimum of about a 3 hour treatment period;
- tissue oxygenation device 200 is capable of circulating the reduced oxygen environment in chamber 208 around the target site 206 during the ambient pressure cycle;
- tissue oxygenation device 200 is capable of keeping a relative humidity over target site 206 at less than about 20% relative humidity;
- tissue oxygenation device 200 is capable of measuring and recording one or more of the following properties as a function of time during treatment periods:
  a. oxygen content in chamber 208 over target site 206 to an accuracy of about ±1%;
  b. the relative humidity in chamber 208 over target site 206;
  c. the pressure over target site 206 within chamber 208 to minimum range limits of about +5 mmHg to about −25 mm Hg;
  d. the temperature of the skin near target site 206; and
  e. skin oxygenation Assembly 300 is further described with reference to its method of use. In an exemplary application and use of assembly 300, leg 206 is inserted within chamber 208, and a seal is created by and between encasement 202 and cuff 204. A computer (not shown) running specially designed software therefrom, is used to sequence and monitor the operation. There are two basic cycles between which tissue oxygenation device 200 alternates: a flush cycle and a negative pressure cycle.

In an exemplary embodiment, a flush cycle begins the operation. Still referring to FIG. 9, the flush cycle includes having a solenoid valve 210 open to allow entry of an oxygen depleting gas into the cycle, wherein an exemplary oxygen depleting gas comprises at least one of nitrogen, helium and the like, wherein nitrogen is particularly preferred.

As shown in FIG. 9, the oxygen depleting gas, which for purposes of illustration only and in this embodiment, consists of nitrogen, enters the cycle from source 212, such as a cylinder, with the assistance of a pressure regulator 214 to reduce the incoming pressure to up to about 10 pounds per square inch ("psi"). The nitrogen gas flows into a recycling loop 216 to flush chamber 208. The flushed gas passes a pressure sensor 218 and an oxygen sensor 220. The flushed gas is moved through and by a continuously running diaphragm pump 222 and through a one way valve 224 into a three way valve 226. Valve 226 is set to "vent" to flush out the flushed gas until oxygen sensor 220 indicates that the oxygen content is less than about 2%, wherein the percentage is based upon the total volume of gas detected by oxygen sensor 220. Once that point is reached, valve 226 switches to "recycle" the oxygen depleted gas around and over target site 206.

Pressure in chamber 208 is monitored by pressure sensor 218 and maintained slightly positive at about +3 mm Hg by opening solenoid valve 210 as necessary. This is to ensure there is no ingress of outside air into chamber 208. Also once the oxygen content rises above about 2% in chamber 208, three-way valve 226 is set to "vent" and solenoid valve 210 is opened until the oxygen is fully purged from chamber 208. Once the oxygen is at or below about 2% then solenoid valve 210 is closed and 3-way valve 226 is set to "recycle" again. For safety purposes a pressure relief valve 228 may be included in the recycle line to ensure that the pressure never exceeds an overpressure setting.

After the flush cycle is completed, a negative pressure cycle may be introduced. In an exemplary negative pressure cycle, as shown in FIG. 9, 3-way valve 226 is set to "vent" and the pump creates a negative pressure in chamber 208. The negative pressure builds until it reaches the desired set point, preferably, about −5 to about −25 mm Hg or less, at which point 3-way valve 226 is set to "recycle". If the pressure rises above the desired set point, then 3-way valve 226 is momentarily set to "vent" until the desired negative pressure level is reached again, at which point 3-way valve 226 is then set to "recycle" once more. If the oxygen content in chamber 208 rises above about 2%, then solenoid valve 210 is opened and 3-way valve 226 is set to "vent" until the oxygen is fully purged from chamber 208. The opening and closing of solenoid valve 210 and 3-way valve 226 is such that the negative pressure level set point is maintained. A relief valve 230 is included in loop 216 to ensure that the negative pressure does not go below safety limits.

At the end of the negative pressure cycle, solenoid valve 210 is opened to allow the nitrogen pressure to rise to about +3 mm Hg, and the flush cycle begins again. In an exemplary embodiment, the programmed treatment ends with a nitrogen flush cycle. Additionally, the nitrogen flush and negative pressure cycles preferably alternate for times previously set in the device program. Nitrogen is consumed in large quantities for the first flush cycle, while only small amounts are required for subsequent flush and negative pressure cycles.

Additionally, assembly 300 comprises a temperature sensor 250 which is positioned within encasement 202 to monitor the temperature of the surrounding area.

In an exemplary embodiment, assembly 300 comprises the following set points and cycle times:

| | |
|---|---|
| Oxygen Setpoint: | approximately ≤2% |
| Nitrogen Flush Cycle time: | approximately 15 minutes |
| Negative Pressure Cycle time: | approximately 15 minutes |
| Pressure during Nitrogen Flush Cycle: | approximately +3 mm Hg |
| Negative pressure level during Negative Pressure Cycle: | maximum level of about −10 to −25 mm Hg |
| Total treatment time: | approximately 3 hours |

Although nitrogen gas is used to purge the oxygen from chamber 208 in the exemplary embodiment discussed above with reference to FIG. 9, other oxygen removing gasses may be used, wherein such gases include, e.g., helium.

Figure 10:
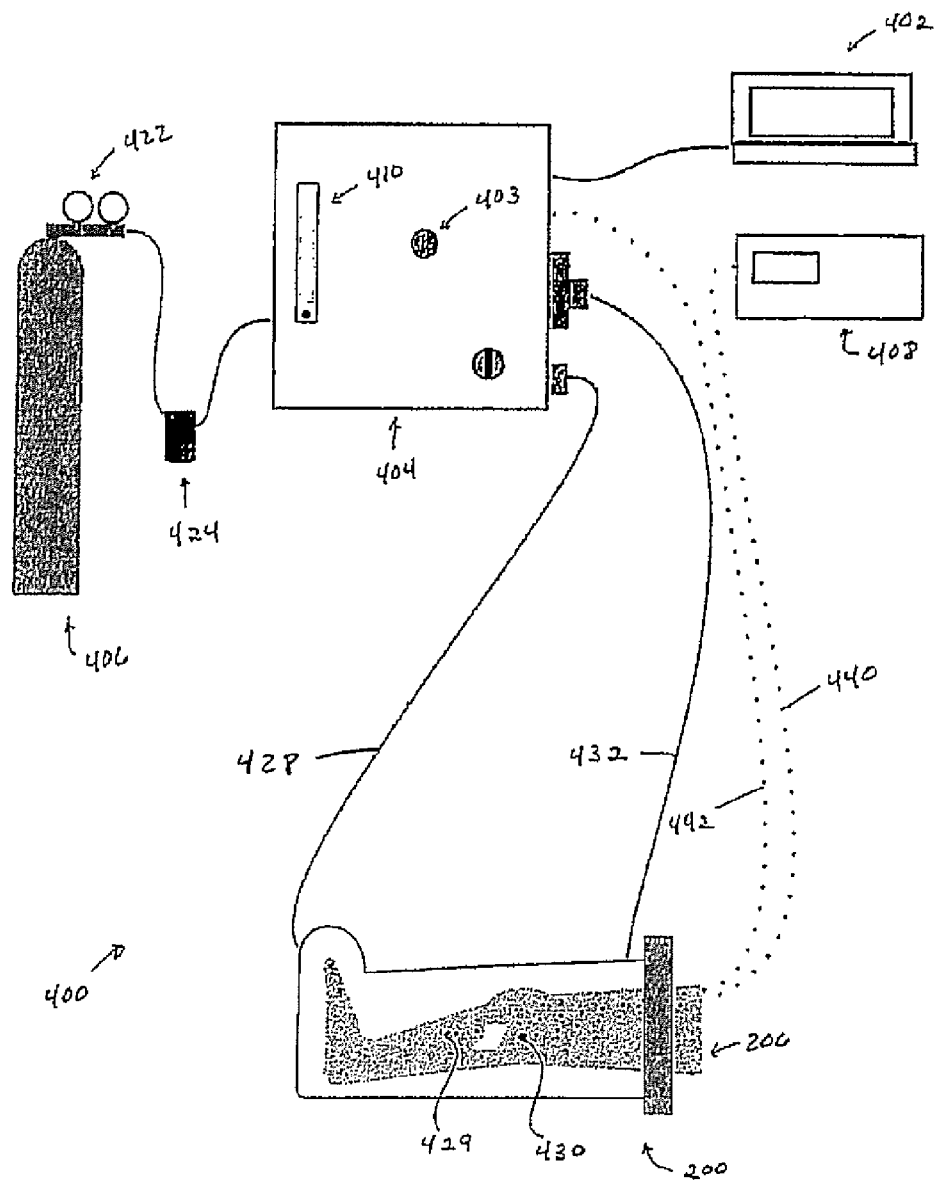
FIGS. 10-11 are schematics depicting another exemplary assembly and its method of use.
Figure 11:
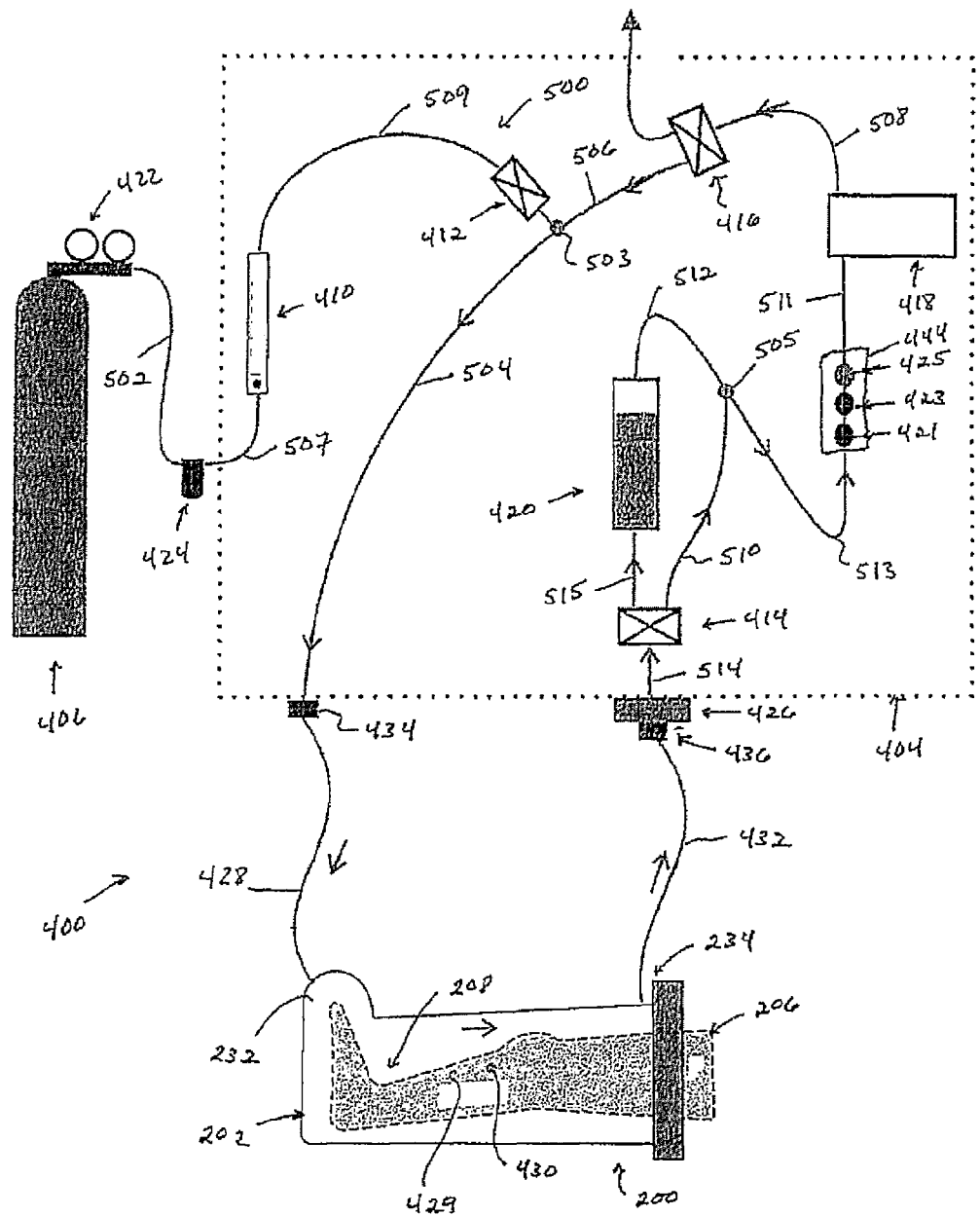

Another exemplary system for creating an oxygen depleted environment immediately over a wound site is depicted in FIGS. 10 and 11. The assembly depicted in FIGS. 10 and 11 is specially designed, e.g., to: (1) create and circulate an oxygen-depleted gas in a confined enclosure over a wound site, thereby creating an oxygen gradient from the capillary bed of the subcutaneous tissue towards the wound site, and thereby promoting oxygen diffusion from the capillary bed to the wound site; (2) further promoting oxygen diffusion through the creation of a negative pressure within the confined enclosure; (3) remove moisture resulting from skin transpiration from the confined enclosure; and (4) measure important variables related to the operation of the system and the condition of the patient, wherein such variables include the temperature of the skin around the wound site, skin oxygenation levels, and the like.

Referring to FIGS. 10 and 11, assembly 400 comprises tissue oxygenation device 200, an oxygen depleting gas source 406, computer 402, and a control box 404. Although the tissue oxygenation device 200 is identical to that disclosed above with reference to FIGS. 1-9, it is contemplated that the tissue oxygenation device may comprise modifications thereto and/or may be configured to fit on an anatomical part other than the leg. Additionally, the tissue oxygenation device may or may not comprise an oxygen scavenger and/or composite as described above with reference to FIGS. 4 and 5, and/or may contain any other oxygen depleting member.

Oxygen depleting gas source 406 contains an oxygen depleting gas which serves to remove oxygen from chamber 208 of tissue oxygenation device 200. Although nitrogen gas shall be used to describe the embodiment depicted in FIGS. 10 and 11, it is to be understood that the invention is not limited to nitrogen, but, rather, may include any suitable oxygen depleting gas, such as, for example, helium.

Computer 402 contains software which is specially programmed to run assembly 400. Control box 404 contains a computer interface, such as, e.g., USB interface, which interfaces with the software run by computer 402. Control box 404 further holds a rotameter 410, a solenoid valve 412, a valve 414, a valve 416, a diaphragm pump 418 which generates the power to move the gas stream though assembly 400, a moisture absorption canister 420 which absorbs excess moisture from the gas stream, a gas temperature and humidity sensor 421, a pressure sensor 423, an oxygen sensor 425, and a power supply (not shown) preferably comprising a 12 V and 24 V DC power supply. All of the working components (except for the power supply) in the control box may be powered by, e.g., about 24 volts direct current ("VDC"), to prevent electrical shock. In a preferred embodiment, control box 404 is non-metallic and does not conduct a significant amount of electricity. Additionally, control box 404's AC to DC power supplies are preferably fused in the event of electrical malfunction in the power supply.

Assembly 400 further comprises a pressure regulator 422, HEPA filters 424 and 426, a transcutaneous oxygen sensor 430, a tissue oxygen measurement instrument 408, and a skin temperature sensor 429. Pressure regulator 422 serves to regulate the pressure of the gas emitted from source 406. In an exemplary embodiment, pressure regulator 422 generates a pressure reading of about 5 psi for the nitrogen gas emitted from source 406. HEPA filters 424 and 426 serve to remove contaminants and impurities, such as, microbial contaminants, from the gas flowing through the system. Transcutaneous oxygen sensor or other tissue oxygenation sensor 430, which is connected to skin measuring oxygen instrument 408 via a lead 440, detects the level of tissue oxygenation in the skin next to the wound site. Skin temperature sensor 429 is connected to control box 404 via a lead 442.

Assembly 400 further comprises a tubing subassembly 500 through which the oxygen depleting gas cycles. In an exemplary embodiment, tubing subassembly 500 comprises a tubing 502 which extends from pressure regulator 422 at one end thereof to HEPA filter 424 at another end thereof, and which is in fluid communication with pressure regulator 422 and filter 424. A tubing 507 extends from filter 424 at one end thereof and from rotameter 410 at an opposite end thereof. Tubing 507 is in fluid communication with filter 424 and rotameter 410. A tubing 509, which is in fluid communication with rotameter 410 and which is attached thereto at a terminal end of tubing 509, extends to and through valve 412 and terminates at an opposite end of tubing 509 to connect to a connector 503. A tubing 504, which is in fluid communication with tubing 509, is attached to a quick connect point 434 at one end thereof and to connector 503 at an opposite end thereof. A tubing 506 is attached at one end thereof to connector 503 and to valve 416 at an opposite end thereof and is in fluid communication with tubing 504.

A tubing 508, which is in fluid communication with valve 416 and with pump 481, extends from valve 416 at one end of tubing 508 and from pump 418 at an oppositely situated end thereof. A tubing 511, which is in fluid communication with pump 418 and with oxygen sensor 425, pressure sensor 423, and temperature and humidity sensor 421, extends from pump 418 and from a housing 444 which contains sensors 425, 423, and 421. A tubing 513, which is in fluid communication with housing 444, extends therefrom at one end of tubing 513 and is connected at an opposite end of tubing 513 to a connector 505.

A tubing 510, which is in fluid communication with valve 414 and with tubing 513, extends from and is connected to valve 414 at an end of tubing 510, and is connected to and extends from connector 505 at an opposite end of tubing 510. A tubing 512, which is in fluid communication with tubing 513, is connected to and terminates at connector 505 at one end thereof and is connected to and terminates at moisture absorption canister 420 at an opposite end thereof. A tubing 515, which is in fluid communication with moisture absorption canister 420 and with valve 414 extends from and is connected to moisture absorption canister at one end of tubing 515, and extends from and is connected to valve 414 at an oppositely situated end of tubing 515. A tubing 514, which is in fluid communication with tubing 515 and 510, is connected to and terminates at valve 414 at one end of tubing 514, and is connected to and terminates at filter 426 at an opposite end of tubing 514.

The assembly shall be further described with reference to its function, and with reference to FIG. 11. In an exemplary embodiment, skin oxygen sensor 430 and skin temperature sensor 429 are positioned onto leg 206. Leg 206 is then contained within chamber 208 of device 200. A posterior tubing 428, which extends from a posterior portion 232 of encasement 202 at one end thereof and which is connected to quick connect point 434 at an oppositely situated end thereof, is in fluid communication with chamber 208 and quick connect point 434. An anterior tubing 432, which is connected to an anterior portion 234 of encasement 202 at one end thereof and which is connected to quick connect point 436 at an opposite end thereof, is in fluid communication with chamber 208 and quick connect 436. Oxygen depleting gas source 406 then may be opened, and assembly 400 may be started via the software run on computer 402.

On startup, assembly 400 is set to a "flush" cycle. Here, solenoid valve 412 opens and nitrogen gas enters from source 406 through pressure regulator 422 which is set to reduce the supply pressure of the nitrogen gas to about 5 psi. The nitrogen passes from pressure regulator 422, and through tubing 502, filter 424, and tubing 507, at which point it enters rotameter 410 which monitors and controls the flow of the nitrogen gas. The nitrogen gas then flows through tubing 509, valve 412, tubing 504, quick connect point 432, and posterior tubing 428 after which it then is directed into chamber 208 where it flushes chamber 208. The flushed gas from chamber 208 then moves through anterior tubing 432, quick connect point 436, filter 426, tubing 514, and through valve 414.

Valve 414 is set so that during the flush cycle the gas stream bypasses moisture adsorption canister 420. Rather, the gas stream moves through tubing 510 and tubing 513, and through housing 444 such that the gas stream passes over oxygen sensor 425, pressure sensor 423, and gas temperature and humidity sensor 421. The flushed air, then passes from housing 444, through tubing 511, pump 418 (which is preferably run continuously throughout the flush cycle), tubing 508, and valve 416. Valve 416 is set to "vent" to flush out the gas stream until oxygen sensor 425 indicates that the oxygen content in the flushed gas stream is approximately 2% or less. At this point valve 416 switches to "recycle", valve 412 closes so that the oxygen depleting gas from source 406 cannot enter tubing subassembly 500, and the oxygen-depleted nitrogen gas recycles over and around the wound area via tubings 506, 504, 428, 432, 514, 515, 512, 513, 511, and 508, and valve 414 is set to direct the flow to moisture absorption canister 420.

Moisture absorption canister 420 adsorbs moisture arising from skin transpiration to maintain the relative humidity percentage ("% RH") in the nitrogen at up to about 20% or less. If for any reason the % RH rises above a set-point, valve 412 opens and valve 416 is set to "vent".

Pressure in chamber 208 may be monitored by pressure sensor 423, and preferably is maintained slightly positive at up to about +2 mm Hg by momentarily opening valve 412 as necessary. This slight pressure is designed to minimize ingress of outside oxygen into chamber 208. However if the oxygen concentration in chamber 208 rises above about 2% in the recycled nitrogen, as sensed by pressure sensor 423, then valve 412 may open, and valve 416 may be set to "vent" to bleed off the excess pressure. In case of malfunction of pressure sensor 423, assembly 400 comprises a "stop" button 403 that may be manually actuated to turn assembly 400 off. Once the oxygen concentration in chamber 208 is at or below about 2%, then valve 412 may close and valve 416 may be set to "recycle" once again.

The above-discussed operation preferably continues until the programmed time, as determined by the software in computer 402, is reached. At that time assembly 400 shuts off and tissue oxygenation device 200, along with sensors 429 and 430, may be removed.

In an exemplary embodiment, operation set points include:

| | |
|---|---|
| Oxygen concentration in the chamber: | up to about 2% or less |
| Nitrogen flow rate into the chamber: | about 5 liters per minute |
| Pressure during Ambient Pressure Nitrogen Cycle: | about +2 mm Hg |
| Total treatment time: | about 3 hours |

It is contemplated that assembly 400 may also include a negative pressure cycle as was disclosed above with reference to assembly 300.

It should be understood that other, obvious structural modifications can be made without departing from the spirit or scope of the invention. Accordingly, reference should be made to the accompanying Claims, rather than the foregoing description, to determine the scope of the invention.

What is claimed is:

1. A method for promoting tissue oxygenation, comprising:
   providing an assembly, comprising:
   a tissue oxygenation device, wherein the tissue oxygenation device comprises a chamber formed within an encasement:
   a first valve, a second valve, a pump, and a tubing subassembly, wherein the tubing subassembly provides a conduit through which an oxygen depleting gas flows through the assembly;
   an oxygen sensor; and
   a pressure sensor;
   applying the tissue oxygenation device to a wound site such that the wound site is enclosed within the chamber;
   providing a source which supplies the oxygen depleting gas to the assembly;
   providing a flush cycle, comprising:
   maneuvering the first valve to allow entry of the oxygen depleting gas into the tubing subassembly from the source;
   actuating the pump to thereby draw the oxygen depleting gas through the first valve and into the chamber via the tubing subassembly, and to further thereby draw the oxygen depleting gas from the chamber and through the second valve via the tubing subassembly;
   maneuvering the second valve to allow entry therein of the oxygen depleting gas received from the tubing subassembly, and to further allow the oxygen depleting gas to vent out of the assembly until an oxygen concentration in the chamber is at an oxygen concentration threshold value;
   recirculating the oxygen depleting gas through the assembly once the oxygen concentration threshold value has been established, wherein the recirculation comprises:
   maneuvering the first valve to prevent the oxygen depleting gas from entering the assembly from the source;
   maneuvering the second valve to prevent further venting of the oxygen deleting gas, and to allow the oxygen depleting gas to circulate through the assembly;

actuating the pump thereby causing the oxygen depleting gas to flow through the assembly; and using the pressure sensor to monitor a pressure in the chamber wherein, when the pressure sensor detects the pressure in the chamber during the flush cycle to be above a pressure threshold level, the first valve is maneuvered to allow ingress of the oxygen depleting gas from the source into the assembly;

having the oxygen sensor monitor the concentration of oxygen in the oxygen depleting gas as the oxygen depleting gas flows through the assembly; and having the oxygen sensor detect when the concentration of oxygen in the oxygen depleting gas flowing in the chamber is greater than about 2 percent based upon a total volume of the gas flowing over the oxygen sensor, wherein, when the oxygen concentration in the oxygen depleting gas flowing in the chamber is greater than about 2 percent, the first valve is maneuvered to allow the oxygen depleting gas to enter the assembly via the source and the second valve is manipulated to allow the oxygen depleting gas to exit the assembly.

2. A method for promoting tissue oxygenation, comprising: providing an assembly, comprising:
 a tissue oxygenation device, wherein the tissue oxygenation device comprises a chamber formed within an encasement; and
 a first valve, a second valve, a pump, and a tubing subassembly, wherein the tubing subassembly provides a conduit through which an oxygen depleting gas flows through the assembly;
 applying the tissue oxygenation device to a wound site such that the wound site is enclosed within the chamber;
 providing a source which supplies the oxygen depleting gas to the assembly;
 providing a flush cycle, comprising:
 maneuvering the first valve to allow entry of the oxygen depleting gas into the tubing subassembly from the source;
 actuating the pump to thereby draw the oxygen depleting gas through the first valve and into the chamber via the tubing subassembly, and to further thereby draw the oxygen depleting gas from the chamber and through the second valve via the tubing subassembly;
 maneuvering the second valve to allow entry therein of the oxygen depleting gas received from the tubing subassembly, and to further allow the oxygen depleting gas to vent out of the assembly until an oxygen concentration in the chamber is at an oxygen concentration threshold value; and
 recirculating the oxygen depleting gas through the assembly once the oxygen concentration threshold value has been established, wherein the recirculation comprises:
  maneuvering the first valve to prevent the oxygen depleting gas from entering the assembly from the source;
  maneuvering the second valve to prevent further venting of the oxygen deleting gas, and to allow the oxygen depleting gas to circulate through the assembly; and
  actuating the pump thereby causing the oxygen depleting gas to flow through the assembly;
 creating a negative pressure in the chamber, wherein the creation of the negative pressure comprises:
 maneuvering the first valve to prevent entry of the oxygen depleting gas into the assembly via the source;
 maneuvering the second valve to allow the oxygen depleting gas to exit the assembly; and
 actuating the pump to form the negative pressure;
 alternating between the flush cycle and the negative pressure cycle; and
 running each flush cycle for about 15 minutes and running each negative pressure cycle for about 15 minutes, wherein the total running time between the alternating flush cycles and negative pressure cycles is about 3 hours.

3. A method for promoting tissue oxygenation, comprising: providing an assembly, comprising:
 a tissue oxygenation device, wherein the tissue oxygenation device comprises a chamber formed within an encasement;
 a first valve, a second valve, a pump, and a tubing subassembly, wherein the tubing subassembly provides a conduit through which an oxygen depleting gas flows through the assembly;
 a third valve;
 a moisture absorption canister; and
 a humidity sensor;
 applying the tissue oxygenation device to a wound site such that the wound site is enclosed within the chamber:
 providing a source which supplies the oxygen depleting gas to the assembly;
 providing a flush cycle, comprising:
 maneuvering the first valve to allow entry of the oxygen depleting gas into the tubing subassembly from the source;
 actuating the pump to thereby draw the oxygen depleting gas through the first valve and into the chamber via the tubing subassembly, and to further thereby draw the oxygen depleting gas from the chamber and through the second valve via the tubing subassembly;
 maneuvering the second valve to allow entry therein of the oxygen depleting gas received from the tubing subassembly, and to further allow the oxygen depleting gas to vent out of the assembly until an oxygen concentration in the chamber is at an oxygen concentration threshold value;
 recirculating the oxygen depleting gas through the assembly once the oxygen concentration threshold value has been established, wherein the recirculation comprises:
  maneuvering the first valve to prevent the oxygen depleting gas from entering the assembly from the source; and
  maneuvering the second valve to prevent further venting of the oxygen deleting gas, and to allow the oxygen depleting gas to circulate through the assembly;
 actuating the pump thereby causing the oxygen depleting gas to flow through the assembly;
 passing the oxygen depleting gas over the humidity sensor so that a relative humidity may be detected;
 determining whether the relative humidity exceeds a relative humidity threshold level;
 manipulating the third valve so that the oxygen depleting gas passes through the moisture absorption canister when the relative humidity exceeds the relative humidity threshold level; and
 manipulating the third valve so the oxygen depleting gas bypasses the moisture absorption canister when the relative humidity does not exceed the relative humidity threshold level.

4. The method of claim 3, wherein the relative humidity threshold level is about 20%.

* * * * *